United States Patent [19]

Irick, Jr. et al.

[11] 4,069,227
[45] Jan. 17, 1978

[54] BIS-HETEROCYCLIC BENZOATE ULTRAVIOLET STABILIZERS AND THEIR USE IN ORGANIC COMPOSITIONS

[75] Inventors: Gether Irick, Jr.; Charles A. Kelly, both of Kingsport, Tenn.

[73] Assignee: Eastman Kodak Company, Rochester, N.Y.

[21] Appl. No.: 657,510

[22] Filed: Feb. 12, 1976

Related U.S. Application Data

[62] Division of Ser. No. 484,843, July 1, 1974, Pat. No. 3,963,738.

[51] Int. Cl.$^2$ ............................................ C07D 249/08
[52] U.S. Cl. .................................................. 260/308 R
[58] Field of Search ..................................... 260/308 R

[56] References Cited

U.S. PATENT DOCUMENTS 3,963,738  6/1976  Irick et al. ...................... 260/307 G

*Primary Examiner*—Raymond V. Rush
*Attorney, Agent, or Firm*—J. Frederick Thomsen; Daniel B. Reece, III

[57] ABSTRACT

The invention relates to bis-heterocyclic benzoate compounds which have been found to be extremely effective ultraviolet stabilizers. The invention also relates to ultraviolet degradable organic compositions containing an amount of a bis-heterocyclic benzoate composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions such as polymers by adding to the polymer melt or dissolved in the polymer dope, coated on the exterior of the shaped or molded article, film or extruded fiber.

2 Claims, No Drawings

BIS-HETEROCYCLIC BENZOATE ULTRAVIOLET STABILIZERS AND THEIR USE IN ORGANIC COMPOSITIONS

This is a division of application Ser. No. 484,843 filed July 1, 1974, now U.S. Pat. No. 3,963,738.

This invention relates to ultraviolet stabilizers and their use in organic compositions. More particularly, the invention relates to bis-heterocyclic benzoate compositions and the stabilization of organic compositions against deterioration resulting from the exposure to light with such bis-heterocyclic benzoate compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions is polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb electromagnetic radiation within the band of 2900 to 4000 A. and when incorporated in various plastic materials such as transparent sheets, the resultant sheet acts as a filter for all of the radiation passing through and will transmit only such radiations as are not absorbed by the sheet and/or the absorbing agent. It is thus possible to screen out undesirable radiations and utilize the resulting transparent sheet as a filter in many technical and commercial applications such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore to provide a more effective and efficient ultraviolet stabilizer for organic compositions susceptible to such degradation would be an advance in the state of the art.

It is therefore an object of the present invention to provide compositions characterized by improved resistance to degradation and deterioration by ultraviolet radiation.

Another object of the present invention is to provide compositions containing bis-heterocyclic benzoate compositions which are resistant to ultraviolet degradation.

A further object of this invention is to provide processes for improving the resistance of organic materials to deterioration and degradation by actinic radiation and especially ultraviolet radiation.

It is a still further object of this invention to provide compositions and processes for improving the resistance of organic materials to deterioration and degradation by actinic radiations including short wave-length visible radiations.

Further objects and advantages of the invention will be apparent to those skilled in the art from the accompanying disclosure and claims.

In accordance with the present invention, organic compositions are provided which are useful as ultraviolet stabilizers. These organic compositions contain a bis-heterocyclic phenyl group connected through a carboxyl group to aromatic rings, which by the "photo-Fries" rearrangement can form hydroxyl groups. The organic compositions of the present invention are aryl esters of heterocyclic aromatic acids having the following structure:

wherein A is a group having the structure

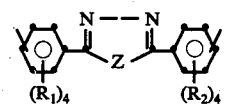

wherein

Z is an oxygen atom, a sulfur atom, a nitrogen atom, or a nitrogen atom containing a hydrogen atom or a substituted or unsubstituted lower alkyl group having 1 to 12 carbon atoms;

$R_1$ and $R_2$ are hydrogen, lower alkyl, substituted lower alkyl, cycloalkyl, substituted cycloalkyl, aryl, substituted aryl, lower alkylaryl, aryl-substituted-aryl, chloro, bromo, alkoxy, alkylsulfonyl, substituted amino, cyano, and at least two adjacent $R_1$ or $R_2$ substituents, combined with the carbon atoms to which they are attached, are joined alkylene groups completing a carbocyclic ring which ring can be substituted with any of the substituents listed above for $R_1$ or $R_2$.

B is an aryl group having the formula

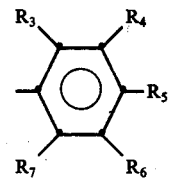

wherein $R_3$, $R_4$, $R_5$, $R_6$ and $R_7$ are hydrogen, lower alkyl, substituted lower alkyl, cycloalkyl, substituted cycloalkyl, aryl, substituted aryl, lower alkylaryl, aryl-substituted-aryl, alkoxy, hydroxy, substituted amino, carboalkoxy, nitrile, chloro, bromo and the substituents $R_3$ and $R_4$, $R_4$ and $R_5$, $R_5$ and $R_6$ and $R_6$ and $R_7$, combined with the carbon atoms to which they are attached, are joined alkylene groups completing a carbocyclic ring which can be substituted with any of the substituents listed above for $R_3$, $R_4$, $R_5$, $R_6$ and $R_7$.

Suitable A groups having the formula

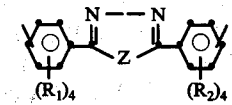

are, for example, substituted and unsubstituted 2,5-diphenyl-1,3,4-oxadiazol-diyl, 2,5-diphenyl-1,3,4-thiadiazol-diyl, and 2,5-diphenyl-1,3,4-triazol-diyl.

Examples of suitable diphenyloxadiazol-diyl moieties are those having the formula

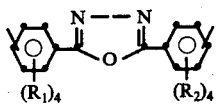

such as 2,5-diphenyl-1,3,4-oxadiazol-3',3''-diyl; 2,5-diphenyl-1,3,4-oxadiazol-4',4''-diyl; 2,5-diphenyl-1,3,4-oxadiazol-3'4''-diyl; 2,5-diphenyl-3',3''-dibromo-1,3,4-oxadiazol-4',4''-diyl; 2,5-diphenyl-3'-methoxy-1,3,4-oxadiazol-4',4''-diyl; 2,5-diphenyl-3'-methyl-1,3,4-oxadiazol-4',3''-diyl; 2,5-diphenyl-3',3'',6',6''-tetrabromo-1,3,4-oxadiazol-4',4''-diyl; and 2,5-diphenyl-3',3'',6',6''-tetramethoxy-1,3,4-oxadiazol-4',4''-diyl.

Examples of suitable diphenylthiadiazol-diyl moieties are those having the formula:

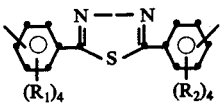

such as 2,5-diphenyl-1,3,4-thiadiazol-3',3''-diyl; 2,5-diphenyl-1,3,4-thiadiazol-4',4''-diyl; 2,5-diphenyl-1,3,4-thiadiazol-3',4'-diyl; 2,5-diphenyl-3',3''-dibromo-1,3,4-thiadiazol-4',4''-diyl; 2,5-diphenyl-3',3''-dichloro-1,3,4-thiadiazol-4',4''-diyl; 2,5-diphenyl-3'-methoxy-1,3,4-thiadiazol-4',4''-diyl; 2,5-diphenyl-3'-methyl-1,3,4-thiadiazol-4',3''-diyl; 2,5-diphenyl-3',3'',6',6''-tetrabromo-1,3,4-thiadiazol-4',4''-diyl; and 2,5-diphenyl-3',3'',6',6''-tetramethoxy-1,3,4-oxadiazol-4',4''-diyl.

Examples of suitable diphenyltriazol-diyl moieties are those having the formula:

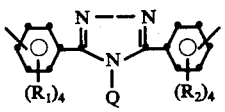

wherein Q is hydrogen or a substituted or unsubstituted lower alkyl group containing 1 to 12 carbon atoms, such as 1-methyl-2,5-diphenyl-1,3,4-triazol-4',4''-diyl; 1-methyl-2,5-diphenyl-3',3''-dibromo-1,3,4-triazol-4',4''-diyl; 1-methyl-2,5-diphenyl-3'-methoxy-1,3,4-triazol-4',4''-diyl; 1-benzyl-2,5-diphenyl-1,3,4-triazol-4',4''-diyl; 1-benzyl-2,5-diphenyl-1,3,4-triazol-3',3''-diyl; 1-benzyl-2,5-diphenyl-3',3'',6',6''-tetrabromo-1,3,4-triazol-4',4''-diyl; 1-ethyl-2,5-diphenyl-1,3,4-triazol-3',4''-diyl; 1-ethyl-2,5-diphenyl-3',3''-dichloro-1,3,4-triazol-4',4''-diyl; 1-ethyl-2,5-diphenyl-3',3''-dimethyl-1,3,4-triazol-4',4''-diyl; 2,5-diphenyl-1,3,4-triazol-4',4''-diyl; and 2,5-diphenyl-1,3,4-triazol-3',3''-diyl.

Examples of aryl B components having the formula:

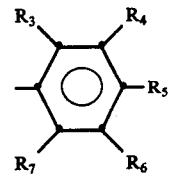

are 2,4-dimethoxyphenyl, 3-methoxyphenyl, 3-methylphenyl, 4-octylphenyl, 4-dodecylphenyl, 3-octylphenyl, 2,4-dichlorophenyl, 4-methoxyphenyl, 2,4-di-t-butylphenyl, 3-(2-ethylhexyloxy)phenyl, 3-dodecyloxyphenyl, 4-cyanophenyl, 4-bromophenyl, 3-hydroxyphenyl and 3-cyclohexylphenyl. The aryl B components can be the same or different.

The bis-heterocyclic benzoate esters can be prepared by reacting the bis-acid chloride with a phenol. For example, one such group of organic compounds useful as ultraviolet stabilizers is bis-heterocyclic benzoate ester-based compositions having the formula

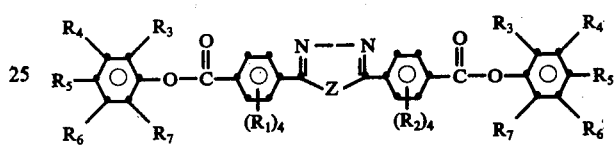

These organic compounds can be prepared according to the following procedure:

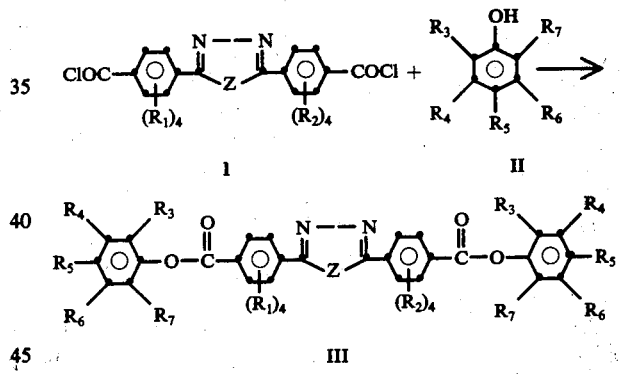

Substituents $R_3$ through $R_7$ are defined hereinabove. It is necessary that at least one of $R_3$ or $R_7$ be hydrogen so that, on exposure to ultraviolet light, the aryl ester of the heterocyclic aromatic acid is capable by the "photo-Fries" rearrangement of forming a phenol group in that position formerly joined through an oxygen atom to the carbonyl linking group, as for example

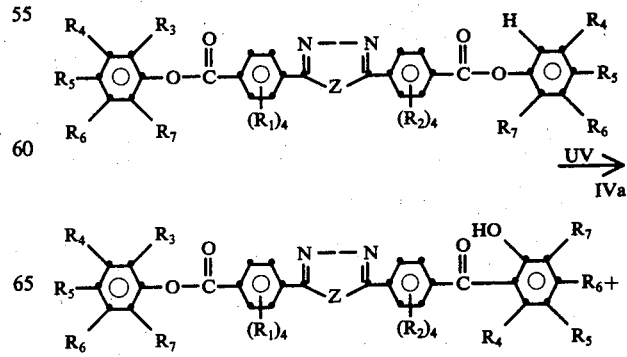

-continued

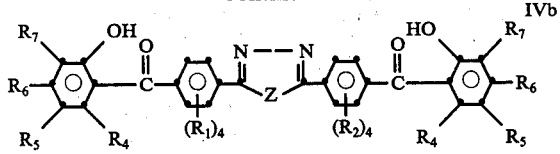

The oxadiazole, thiadiazole and triazole ring systems are generally prepared by procedures discussed and references noted in "Heterocyclic Compounds", R. C. Elderfield, Ed., Wiley, New York, pp. 384–626. The following procedures illustrate typical reaction sequences:

Procedure 1

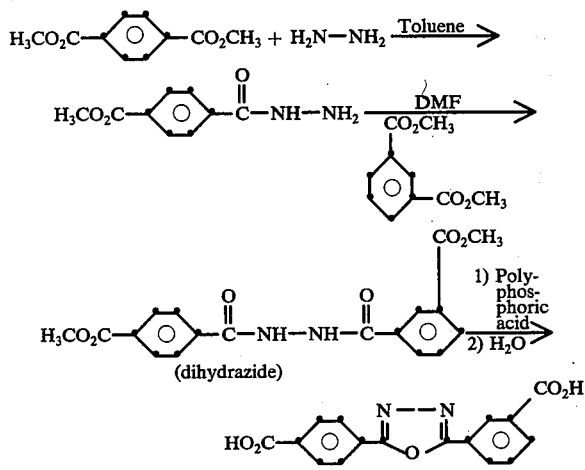

Procedure 2

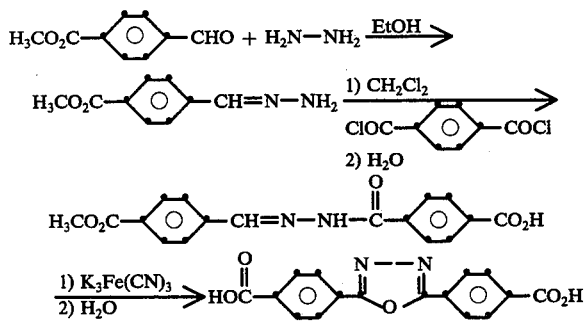

Procedure 3

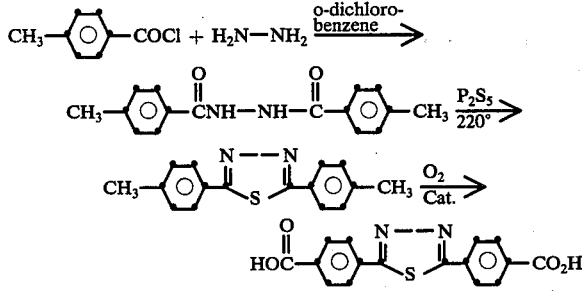

The acid chlorides (I) were prepared by reaction of the corresponding acid [See *Zh. Obshch. Khim.*, 38, 100 1–5 (1968); *Chem. Abstr.* 69, 96568 (1968)] with freshly distilled thinyl chloride [See *J. Chem. Soc.* 101, 2476 (1912)]. The phenols were obtained from commercial sources, or were prepared by standard methods; a critical requirement is that one of the positions adjacent to the phenolic hydroxyl group can be unsubstituted. It is believed that the "photo-Fries" rearrangement can occur upon ultraviolet exposure of the esters III and that these rearrangement products IVb are effective stabilizers.

The bis-heterocyclic benzoate compositions can be added to organic compositions which are susceptible to ultraviolet degradation. Such compositions include, for example, polymeric compositions such as polyester fiber and moldable compositions, such as poly(ethylene terephthalate), poly(tetramethylene terephthalate) and the like; unsaturated polyesters; polyolefins such as, for example, high, medium and low density polyethylene, polypropylene, polybutene and the like; polyamides such as nylon 6, nylon 66 and the like; polycarbonates; poly(vinyl chloride); cellulose esters; cellulose ethers; acrylic/butadiene/styrene plastics; acrylics such as poly(methyl methacrylate); polystyrene; and gelatin. Such compositions also include natural and synthetic rubbers such as polybutadiene, and unsaturated organic compositions such as oils and the like, as well as compositions containing such organic compositions.

The bis-heterocyclic benzoate compositions as effective ultraviolet stabilizers or screening agents are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and deleterious effect which such concentrations may have on the mechanical properties of the organic composition in which the stabilizer is incorporated. Preferably, the stabilizer is used in an amount of from about 0.1 to about 5%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These bis-heterocyclic benzoate ultraviolet stabilizers may be incorporated into organic compositions by melt-blending or may be added onto the surface of an organic plastic material prior to being molded into a suitable object, or added to the surface of the molded object. These materials can also be added to coatings and the like which can be applied to the surface of a molded object.

This invention will be further illustrated by the following examples, although it will be understood that these examples are included merely for purposes of illustration and are not intended to limit the scope of the invention.

EXAMPLE 1

Di-3-methoxyphenyl 2,5-diphenyl-1,3,4-oxadiazol-4′,4″-dicarboxylate

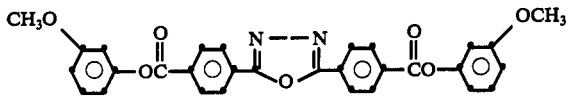

A solution of 3.2 g. hydrazine in 50 ml. dimethylformamide (DMF) was added in 30 minutes to a 120° mixture of 50 g. dimethyl terephthalate in 300 ml. DMF. After stirring for 1 hour, the mixture was poured into 1000 ml. water and the crude dihydrazide collected by filtration. Recrystallization was from DMF/water. Heating the dihydrazide (30 g.) in 200 ml. polyphosphoric acid at 220°, followed by pouring onto ice and heating on a steam bath, gave 12 g. of the intermediate oxadiazole di-acid. Heating the acid (12 g.) with thionyl chloride (50 ml.), removal of excess thionyl chloride by distillation and reaction with 10 g. 3-methoxyphenol in 100 ml. o-dichlorobenzene gave 12 g. of the subject compound, a light tan solid.

EXAMPLE 2

Di-2,4-di-t-butylphenyl 2,5-diphenyl-1,3,4-oxadiazol-4',4''-dicarboxylate

Reaction of the acid (12 g.) prepared as in Example 1 with thionyl chloride, followed by reaction in o-dichlorobenzene with 15 g. 2,4-di-t-butylphenol afforded, after recrystallization from methyl cellosolve, 12 g. nearly colorless product.

EXAMPLE 3

Di-4-tert-octylphenyl 2,5-diphenyl-1,3,4-oxadiazol-4',4''-dicarboxylate

Reaction of the acid (12 g.) prepared as in Example 1 with thionyl chloride, followed by reaction in o-dichlorobenzene with 30 g. 4-tert-octylphenol afforded, after recrystallization from o-xylene, 18 g. colorless product.

EXAMPLE 4

Di-3-methoxyphenyl 2,5-diphenyl-1,3,4-thiadiazol-4',4''-dicarboxylate

A mixture of the dihydrazide (30 g.) prepared as in Example 1, and phosphorus pentasulfide was heated at 220° C./10 mm. pressure, followed by cooling and stirring on a steam bath in 4% sulfuric acid (300 ml.). Filtration, water-washing and drying afforded 16 g. of the intermediate thiadiazole di-acid. The acid (16 g.) was reacted with 75 ml. thionyl chloride, followed by distillation to remove excess thionyl chloride. Reaction of the resulting di-acid chloride with 15 g. 3-methoxyphenol in 250 ml. o-dichlorobenzene gave, after recrystallization from methyl cellosolve, 22 g. nearly colorless solid.

Other bis-heterocyclic benzoate compounds, such as bis-oxadiazoles, bis-thiadiazoles and bis-thiazoles, can be prepared by this procedure by using the appropriate acids and substituted or unsubstituted phenols. Weathering data obtained by the use of several such bis-heterocyclic benzoate compounds is shown in following table.

| Typical Weathering Data for 1/16" Thick Poly(tetramethylene terephthalate) Flat Bars Containing 1% of The Compounds of this Invention | | | |
|---|---|---|---|
| | Flatwise Impact Strength After Mercury Lamp Exposure For Hours Indicated | | |
| Compound | 0 | 300 | 500 |
| Di-3-methoxyphenyl 2,5-diphenyl-1,3,4-oxadiazol-3',3''-dicarboxylate | 18 | 18 | 18 |
| Di-2,4-dichlorophenyl 2,5-diphenyl-1,3,4-oxadiazol-4',4''-dicarboxylate | 17 | 18 | 17 |
| Di-4-t-octylphenyl 2,5-di phenyl-1,3,4-oxadiazol-3',4''-dicarboxylate | 20 | 19 | 18 |
| Di-2,5-diphenyl-3',3'',6',6''-tetramethoxy-1,3,4-oxadiazol-4',4''-dicarboxylate | 19 | 19 | 18 |
| Di-4-phenylphenyl 2,5-diphenyl-1,3,4-oxadiazol-4',4''-dicarboxylate | 18 | 17 | 17 |
| Di-3-methylphenyl 2,5-diphenyl-1,3,4-thiadiazol-4',4''-dicarboxylate | 19 | 19 | 17 |
| Di-4-cyanophenyl 2,5-diphenyl-1,3,4-thiadiazol-1,3,4-thiadiazol-3',4''-dicarboxylate | 19 | 18 | 18 |
| Di-3-phenoxyphenyl 2,5-diphenyl-1,3,4-thiadiazol-3',3''-dicarboxylate | 20 | 18 | 18 |
| Di-2,4-di-t-butyl-phenyl 2,5-diphenyl-3',3''-dichloro-1,3,4-thiadiazol-4',4''-dicarboxylate | 19 | 17 | 17 |
| Di-3,5-di-t-butyl-4-hydroxyphenyl 2,5-diphenyl-1,3,4-thiadiazol-4',4''-dicarboxylate | 19 | 18 | 18 |
| Di-3-methoxyphenyl 1-methyl-2,5-diphenyl-1,3,4-triazol-4',4''-dicarboxylate | 18 | 18 | 17 |
| Di-4-chlorophenol 1-benzyl-2,5-diphenyl-3',3''-dichloro-1,3,4-triazol-4',4''-dicarboxylate | 20 | 17 | 17 |
| Di-4-phenylphenyl 1-methyl-2,5-diphenyl-1,3,4-triazol-3',3''-dicarboxylate | 20 | 19 | 16 |
| Di-2,4-dichlorophenyl 1-ethyl-2,5-diphenyl-1,3,4-triazol-4',4''-dicarboxylate | 17 | 17 | 17 |
| Di-3,4,5-trimethylphenyl 2,5-diphenyl-1,3,4-triazol-3',3''-dicarboxylate | 19 | 17 | 16 |

These diesters of bis-heterocyclic aromatic acid compositions find particular utility as ultraviolet stabilizers in organic compositions requiring ultraviolet stability. Such compositions include polymeric compositions such as, for example, polyester fiber and molding compositions; poly-α-olefins; polyamides; acrylics; cellulose esters and the like, as well as molded or shaped articles, film and coatings formed from such materials, and the like. Such compositions also include natural and synthetic rubbers, such as natural rubber, as well as organic materials such as oils, fats, and unsaturated organic materials, and materials having such materials contained therein, such as paints, varnishes, cosmetics and the like.

The invention has been described in detail with particular reference to preferred embodiments thereof, but it will be understood that variations and modifications can be effected within the spirit and scope of the invention.

We claim:
1. A composition of matter having the formula:

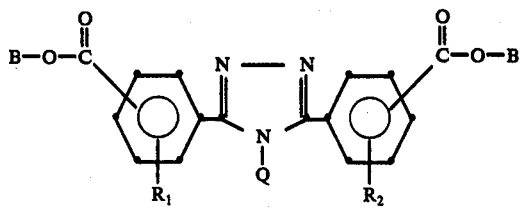

wherein

Q is hydrogen, lower alkyl having 1 to 12 carbon atoms, or benzyl;

$R_1$ and $R_2$ are hydrogen, chloro, or bromo; and

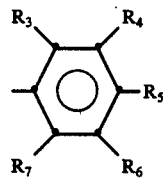

is attached to the benzenoid ring in either the meta or para position from the carbon atom connected to the heterocyclic ring; and B is a group having the formula

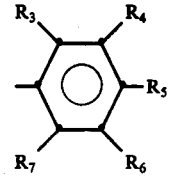

wherein at least one $R_3$ is hydrogen and the other $R_3$, $R_4$, $R_5$, $R_6$ and $R_7$ of each B group are hydrogen, or at the most two substituents selected from lower alkyl, hydroxy, chloro and bromo.

2. A composition of matter having the formula

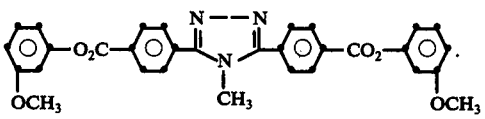

* * * * *

UNITED STATES PATENT OFFICE
CERTIFICATE OF CORRECTION

Patent No. 4,069,227  Dated January 17, 1978

Inventor(s) Gether Irick, Jr. and Charles A. Kelly

It is certified that error appears in the above-identified patent and that said Letters Patent are hereby corrected as shown below:

Column 9, lines 19-26, delete the formula and insert therefor $$--- B-O-\overset{O}{\underset{\|}{C}} ---.$$

Signed and Sealed this

Ninth Day of May 1978

[SEAL]

Attest:

RUTH C. MASON
Attesting Officer

LUTRELLE F. PARKER
Acting Commissioner of Patents and Trademarks